United States Patent
Cho et al.

(10) Patent No.: US 11,898,164 B2
(45) Date of Patent: Feb. 13, 2024

(54) METHOD FOR PRODUCING PLURIPOTENT STEM CELL-DERIVED SPHERICAL NEURAL MASS HAVING SUPPRESSED TERATOMA FORMATION

(71) Applicant: JEIL PHARMACEUTICAL CO., LTD., Seoul (KR)

(72) Inventors: Myung Soo Cho, Seoul (KR); Mi Sun Lim, Gyeonggi-do (KR); So Yeon Ji, Chungcheongbuk-do (KR)

(73) Assignee: S.BIOMEDICS CO., LTD., Seoul (KR)

(*) Notice: Subject to any disclaimer, the term of this patent is extended or adjusted under 35 U.S.C. 154(b) by 625 days.

(21) Appl. No.: 16/474,662

(22) PCT Filed: Dec. 20, 2017

(86) PCT No.: PCT/KR2017/015110
§ 371 (c)(1),
(2) Date: Jun. 28, 2019

(87) PCT Pub. No.: WO2018/124605
PCT Pub. Date: Jul. 5, 2018

(65) Prior Publication Data
US 2019/0330590 A1    Oct. 31, 2019

(30) Foreign Application Priority Data

Dec. 30, 2016 (KR) ........................ 10-2016-0184325

(51) Int. Cl.
*C12N 5/00* (2006.01)
*C12N 5/0793* (2010.01)
*C12N 5/0797* (2010.01)

(52) U.S. Cl.
CPC ......... *C12N 5/0619* (2013.01); *C12N 5/0623* (2013.01); *C12N 2501/115* (2013.01); *C12N 2506/08* (2013.01); *C12N 2506/45* (2013.01); *C12N 2533/20* (2013.01); *C12N 2533/52* (2013.01); *C12N 2533/54* (2013.01); *C12N 2533/90* (2013.01)

(58) Field of Classification Search
CPC ............... C12N 5/0619; C12N 5/0623; C12N 2501/115; C12N 2506/08; C12N 2506/45; C12N 2533/20; C12N 2533/52; C12N 2533/54; C12N 2533/90; C12N 5/0062; C12N 2501/11; C12N 2506/02; C12N 5/00; C12N 5/0622; C12N 5/0068; C12N 2501/50; C12N 2533/50
See application file for complete search history.

(56) References Cited

U.S. PATENT DOCUMENTS

| | | |
|---|---|---|
| 8,492,149 B2 | 7/2013 | Cho et al. |
| 8,921,107 B2 | 12/2014 | Moon |
| 9,005,975 B2 | 4/2015 | Okano et al. |
| 10,231,999 B2 | 3/2019 | Lee et al. |
| 2010/0317103 A1 | 12/2010 | Cho et al. |
| 2011/0250236 A1 | 10/2011 | Lopez Barneo et al. |
| 2013/0089926 A1 | 4/2013 | Moon |
| 2017/0266235 A1 | 9/2017 | Lee et al. |
| 2021/0115399 A1 | 4/2021 | Sasai et al. |

FOREIGN PATENT DOCUMENTS

| | | |
|---|---|---|
| JP | 2009-268433 A | 11/2009 |
| KR | 10-2007-0117440 A | 12/2007 |
| KR | 10-2011-0136061 A | 12/2011 |
| KR | 10-2015-0145891 A | 12/2015 |
| KR | 10-1783977 B1 | 10/2017 |
| WO | 2009/016262 A1 | 2/2009 |
| WO | 2010/137348 A1 | 12/2010 |
| WO | 2011/055855 A1 | 5/2011 |
| WO | 2016/032151 A1 | 3/2016 |

OTHER PUBLICATIONS

Component Concentration sheet for culture medium supplements published online Sep. 29, 2017, Retrieved online from <https://www.frontiersin.org/files/Articles/294420/fnmol-10-00305-HTML/image_m/fnmol-10-00305-t001.jpg> Retrieved on: [Apr. 13, 2019 12:56:38 PM] (Year: 2017).*
Ghasemi-Dehkordi et al., J. Cell Commun. Signal. (2015) 9:233-246 (Year: 2015).*
Zhang et al., J. Neurosci. Res. 59, 421-429, 2000 (Year: 2000).*
Kanemura et al., Musashi1, an evolutionarily conserved neural RNA-binding protein is a versatile marker of human glioma cells in determining their cellular origin, malignancy and proliferative activity, Differentiation, 68 (2001), pp. 141-152 (Year: 2001).*
Lendahl et al., CNS stem cells express a new class of intermediate filament protein, Cell, 60 (1990), pp. 585-595 (Year: 1990).*
D. Amndola et al., Stem Cell Res. & Therapy, 5(55):1-18 (2014).
Y. Okada et al., Stem Cells, 26: 3086-3098 (2008).
S. Woo et al., BMC Neuroscience, 10(97): 1-12 (2009).
P. Hall et al., BMC Neuroscience, 9(71): 1-10 (2008).
A. Gentilella et al., Cell Cycle, 9(20): 4245-4247 (2010).
M. Toda et al., Inflammation and Regeneration, 22(5): 469-473 (2002).

* cited by examiner

*Primary Examiner* — Kimberly Ballard
*Assistant Examiner* — Stacey N Macfarlane
(74) *Attorney, Agent, or Firm* — Norris McLaughlin, P.A.

(57) ABSTRACT

Disclosed is a method for producing a spherical neural mass having suppressed teratoma formation. When using the spherical neural mass produced according to the method of the present disclosure, the purity of the neuronal progenitor cells may be improved, the teratoma formation may be suppressed, and the viability and recovery percentage of the cell may be increased.

10 Claims, 4 Drawing Sheets
Specification includes a Sequence Listing.

A In direct enzyme-based treatment of SNM

B In enzyme-based treatment of SNM fragment after physical fragmentation and subsequent adhesion-culturing Immediately after treatment

Cell viability : 80.5%+79.3%=159.8% Average 79.9%

Immediately after treatment

Cell viability : 90.7%+90.1%=180.8% Average 90.4%

Recovery percentage after one day culture

Cell viability : 55%+57.9%=112.9% Average 56.45%

Recovery percentage after one day culture

Cell viability : 82.4%+76.8%=159.2% Average 79.6%

A Comparison of expressions of undifferentiated pluripotent stem cell markers (SSEA-4, TRA1-60)

B Comparison of expressions of neuronal progenitor cell markers (Musashi, Pax6)

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Gapdh F

<400> SEQUENCE: 1
accacagtcc atgccatcac                    20

<210> SEQ ID NO 2
<211> LENGTH: 19
<212> TYPE: DNA
<213> ORGANISM: Artificial seqence
<220> FEATURE:
<223> OTHER INFORMATION: Gapdh R

<400> SEQUENCE: 2
tccaccaccc tgttgctgt                     19

<210> SEQ ID NO 3
<211> LENGTH: 22
<212> TYPE: DNA
<213> ORGANISM: Artificial sequence
<220> FEATURE:
<223> OTHER INFORMATION: 04-Oct F

<400> SEQUENCE: 3
cgttctcttt ggaaaggtgt tc                 22

<210> SEQ ID NO 4
<211> LENGTH: 20
<212> TYPE: DNA
<213> ORGANISM: Artificial Sequence
<220> FEATURE:
<223> OTHER INFORMATION: 04-Oct R

<400> SEQUENCE: 4
acactcggac cacgtctttc                    20

<210> SEQ ID NO 5
<211> LENGTH: 23
<212> TYPE: DNA
<213> ORGANISM: Artificial Sequence
<220> FEATURE:
<223> OTHER INFORMATION: Nanog F

```
<400> SEQUENCE: 5
gcgtacgcaa attaaagtcc aga                                          23

<210> SEQ ID NO 6
<211> LENGTH: 20
<212> TYPE: DNA
<213> ORGANISM: Artificial Sequence
<220> FEATURE:
<223> OTHER INFORMATION: Nanog R

<400> SEQUENCE: 6
tgctattctt cggccagttg                                              20

<210> SEQ ID NO 7
<211> LENGTH: 20
<212> TYPE: DNA
<213> ORGANISM: Artificial Sequence
<220> FEATURE:
<223> OTHER INFORMATION: Pax6 F

<400> SEQUENCE: 7
ggcaacctac gcaagatggc                                              20

<210> SEQ ID NO 8
<211> LENGTH: 20
<212> TYPE: DNA
<213> ORGANISM: Artificial Sequence
<220> FEATURE:
<223> OTHER INFORMATION: Pax6 R

<400> SEQUENCE: 8
tgagggctgt gtctgttcgg                                              20

<210> SEQ ID NO 9
<211> LENGTH: 20
<212> TYPE: DNA
<213> ORGANISM: Artificial Sequence
<220> FEATURE:
<223> OTHER INFORMATION: Sox1 F

<400> SEQUENCE: 9
caatgcgggg aggagaagtc                                              20

<210> SEQ ID NO 10
<211> LENGTH: 20
<212> TYPE: DNA
<213> ORGANISM: Artificial Sequence
<220> FEATURE:
<223> OTHER INFORMATION: Sox1 R

<400> SEQUENCE: 10
ctctggacca aactgtggcg                                              20

<210> SEQ ID NO 11
<211> LENGTH: 21
<212> TYPE: DNA
<213> ORGANISM: Artificial Sequence
<220> FEATURE:
<223> OTHER INFORMATION: Nestin F

<400> SEQUENCE: 11
cagctggcgc acctcaagat g                                            21

<210> SEQ ID NO 12
```

```
<211> LENGTH: 23
<212> TYPE: DNA
<213> ORGANISM: Artificial Sequence
<220> FEATURE:
<223> OTHER INFORMATION: Nestin R

<400> SEQUENCE: 12
agggaagttg ggctcaggac tgg                                              23

<210> SEQ ID NO 13
<211> LENGTH: 22
<212> TYPE: DNA
<213> ORGANISM: Artificial Sequence
<220> FEATURE:
<223> OTHER INFORMATION: NF-M F

<400> SEQUENCE: 13
gagcgcaaag actacctgaa ga                                               22

<210> SEQ ID NO 14
<211> LENGTH: 23
<212> TYPE: DNA
<213> ORGANISM: Artificial Sequence
<220> FEATURE:
<223> OTHER INFORMATION: NF-M R

<400> SEQUENCE: 14
cagcgatttc tatatccaga gcc                                              23
```

METHOD FOR PRODUCING PLURIPOTENT STEM CELL-DERIVED SPHERICAL NEURAL MASS HAVING SUPPRESSED TERATOMA FORMATION

CROSS-REFERENCE TO RELATED APPLICATIONS

This application is based on and claims priority from Korean Patent Application No. 10-2016-0184325, filed on Dec. 30, 2016, with the Korean Intellectual Property Office, the disclosure of which is incorporated herein in its entirety by reference.

TECHNICAL FIELD

The present disclosure relates to a method for producing a spherical neural mass having suppressed teratoma formation from a pluripotent stem cell.

BACKGROUND

A pluripotent stem cell is a cell that can proliferate infinitely while maintaining its undifferentiated state and can be differentiated into specific functional cell types under certain environments and conditions. Human pluripotent stem cells may undergo infinite proliferation (self-renewal) under appropriate culture conditions and may be differentiated into all kinds of cells that constitute an entity. Therefore, studies are being conducted on various aspects such as understanding of basic knowledge about development, differentiation and growth of an entity, and development of a therapeutic agent for treating a disease or damage of the entity.

An embryonic stem cell as one of the pluripotent stem cell types may self-renew to produce the same cells indefinitely, unlike differentiated cells having stopped cell division. The embryonic stem cell is capable of being differentiated into all kinds of functional cell types of a body via various environments or stimuli. Therefore, when a cell or an organ is damaged, specific differentiated cells derived from the embryonic stem cells can be used for replacement of the damaged cells or organs. Thus, treatment with the embryonic stem cells derivatives has emerged as a fundamental therapeutic method for various intractable diseases.

Human induced pluripotent stem cells (iPSCs), one of the pluripotent stem cell types, are produced by some reprogramming techniques such as gene modification or extracellular factor treatment. Like the embryonic stem cells, iPSC also may self-renew and may be differentiated into all kind of the cell types in the body. To date, induced pluripotent stem cells (iPSCs) have substantially the same characteristics as the embryonic stem cells, which are pluripotent stem cells, in terms of gene expression and differentiation potential.

Specific differentiated cells derived from human pluripotent stem cells, including neuronal progenitor cells, may be isolated by a fluorescence activated cell sorting (FACS) or a magnetic activated cell sorting (MACS) using each unique surface marker expressed from the specific differentiated cell. However, in the MACS, a isolation purity is relatively low without a high recovery rate. In some cases, in the MACS, deformation may occur due to a magnetic material. FACS has a disadvantage that the FACS may damage cells due to a laser. Further, when it is intended to separate differentiated cells derived from the pluripotent stem cells, both MACS and FACS have the potential that undifferentiated pluripotent stem cells may be mixed with the differentiated pluripotent stem cells. Thus, in both MACS and FACS, there is a technical limitation in separating only the differentiated cells at a 100% purity. Thus, the possibility of teratoma formation in the cell therapy agent developed using the pluripotent stem cells may not be excluded. Thus, there is a need to develop a technique for selectively removing the undifferentiated pluripotent cells having a risk of teratoma formation from the differentiated cell populations, while non-affecting the differentiated cells. This selective removal technique is essential for clinical test and commercialization of the pluripotent stem cell-derived cell therapies.

Further, in using negative selection, antibodies against human pluripotent stem cell transcription factors Oct-4, Nanog and Sox-2, and cell surface markers TRA-1-60, TRA-1-81, SSEA3 and SSEA4, have been used to separate and remove the pluripotent stem cells from the differentiated cell populations. However, it has been reported that most of the factors or markers have a carbohydrate epitope or a function thereof is not essential to self-reproduction or pluripotent maintenance of the human pluripotent stem cells. Thus, it may not be guaranteed that only the undifferentiated pluripotent stem cells are correctly and selectively removed using the factors or markers. Further, there is a method of natural death of undifferentiated cells at a specific time by manipulation of gene. However, this gene manipulation method has a disadvantage that its efficiency is low and its safety is not verified.

SUMMARY

The present inventors have studied to find a method for having suppressed teratoma formation in the production of pluripotent stem cell-derived neuronal progenitor cells. From this study, it was confirmed that the teratoma formation suppressing method according to the present disclosure naturally removes undifferentiated pluripotent stem cells during culturing and blocks the possibility of teratoma formation.

A purpose of the present disclosure is to provide a method for producing a spherical neural mass derived from a pluripotent stem cell, the mass having the suppressed teratoma formation.

An exemplary embodiment of the present disclosure provides a method for producing spherical neural masses having suppressed teratoma formation, the method including: performing single-cellularization of spherical neural masses; spontaneously re-aggregating the neuronal progenitor cells single-cellularized; and recovering the spherical neural masses as re-aggregated.

Another exemplary embodiment of the present disclosure provides a spherical neural mass having suppressed teratoma formation, the mass being produced by the method defined above.

Yet another exemplary embodiment of the present disclosure provides a method for differentiating spherical neural mass into neuronal cells including differentiating the spherical neural masses.

According to the exemplary embodiments of the present disclosure, the method for producing the spherical neural mass may improve the purity of the neuronal progenitor cells produced, may suppress the formation of teratoma, and may increase the viability and recovery percentage of the cell.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

The present disclosure is described in detail below.

The present disclosure provides a method for producing spherical neural masses having suppressed teratoma formation, the method including: 1) performing single-cellularization of spherical neural masses; 2) re-aggregating the spherical neural masses single-cellularized in the step 1); and 3) recovering the spherical neural masses re-aggregated in the step 2).

Figure 1:
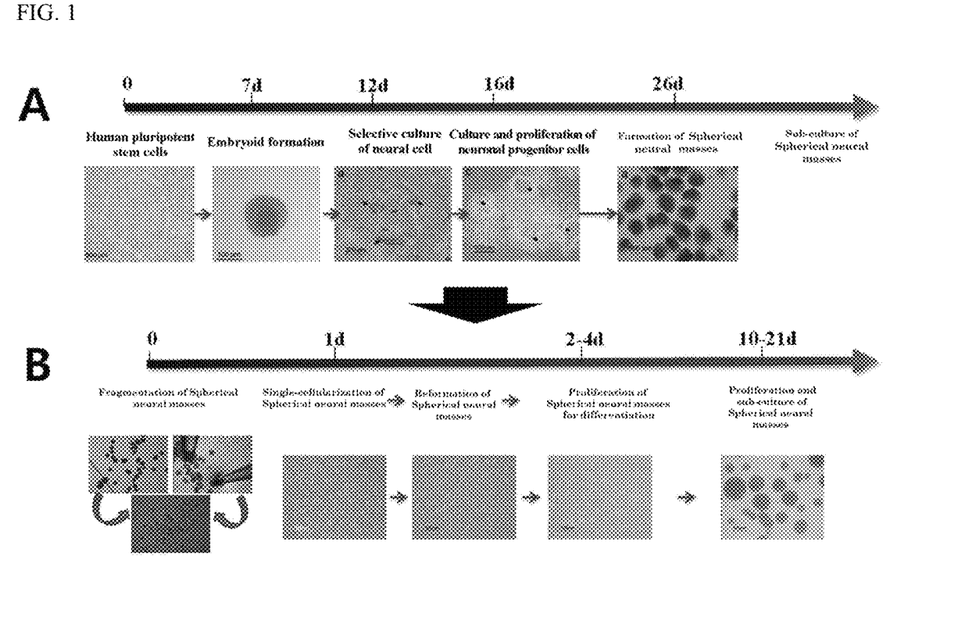
FIG. 1 compares a conventional method (A) and a present method (B) for producing spherical neural masses according to the present disclosure.

FIG. 1 compares a conventional method (A) and a present method (B) for producing spherical neural masses according to the present disclosure.

As used herein, a term "spherical neural mass" means that neuronal progenitor cells derived from pluripotent stem cells, such as human embryonic stem cells or induced pluripotent stem cells, or neuronal progenitor cells isolated from neuronal tissue, are aggregated into a spherical shape.

In the production method, a culturing medium for the cell may be a medium supplemented with N-2 supplement, bFGF or a mixture thereof.

As used herein, a term "N-2 supplement" is a serum-free supplement chemically defined based on Bottenstein's N-1 formulation. The N-2 supplement may be added to the culturing medium supplemented with growth factors such as bFGF and EGF for growth and expression of neuronal cells and neuroblastoma after the primary culturing differentiation of the peripheral neuronal system and the central neuronal system.

The N-2 supplement may be added in an amount of 0.5 to 2.0% (v/v), more specifically, 1.0 to 1.5% (v/v) based on a total volume of a neuronal progenitor cell culturing medium. When the content of the N-2 supplement is smaller than 0.5% (v/v), the cell growth efficiency may be lowered. When the content of the N-2 supplement is above 2.0% (v/v), the maintenance of the cell culturing may be difficult due to proliferation resulting from excessive nutrient. According to one embodiment of the present disclosure, the content of the N-2 supplement may be 1% (v/v) relative to the total volume of the neuronal progenitor cell culturing medium.

As used herein, a term "bFGF (basic fibroblast growth factor)" refers to a strong mitotic stimulating factor for both normal fibroblasts and established cell lines. The bFGF may have functions such as cell migration, formation of new blood vessels, maintenance of neuronal cells, regulation of endocrine function, expression of specific cellular proteins, promotion of extracellular matrix production and cell survival.

The bFGF may be added in a content of 0.0002 to 0.001% (w/v), more specifically 0.0006 to 0.0008% (w/v) based on the total mass of the medium for neuronal progenitor cell culturing. If the content of bFGF is smaller than 0.0002% (w/v), the efficiency of cell growth and division may be decreased. If the content is over 0.001% (w/v), excessive proliferation may lead to cell culturing problem. According to one embodiment of the present disclosure, the content of the bFGF may be 0.00063% (w/v) relative to the total mass of the medium for neuronal progenitor cell culturing.

The step 1) culturing and step 3) culturing may be performed in a culturing dish having a substrate coated thereon. The substrate may be any one or more selected from a group consisting of laminin, L-ornithine, Matrigel and CeLLstart. In one embodiment according to the present disclosure, the substrate may be Matrigel.

To re-aggregate spherical neural masses, the aggregating force of the spherical neural masses must be stronger than the attaching force between the spherical neural masses and the culturing dish. Therefore, unlike the step 1) and 3), in the step 2), the spherical neural masses can be re-aggregated using a culturing dish without a substrate coated thereon. Single-cellularization in the step 1) may involve fragmentation of the spherical neural masses using a micro fragmentation tool. In this connection, when the fragmentation is performed using a cell separation enzyme, the cell is damaged and therefore the recovery percentage is small. Thus, a physical fragmentation may be used. A tool for physical fragmentation may include any tool that can cut the mass of a diameter of 500 μm or smaller under a dissecting microscope. Specifically, the tool may include a tool fabricated by finely drawing a glass Pasteur pipette, a metal wire having a diameter of 100 μm or smaller, and a metal mesh having a hole with a micrometer (μm). According to one embodiment of the present disclosure, the fragmentation may be performed using the tool fabricated by finely drawing a glass Pasteur pipette.

Further, the fragmented spherical neural masses may be subjected to single-cellularization using, as an enzyme for cell separation, enzymes well known in the art, such as trypsin-EDTA, dispase, accutase and collagenase. According to one embodiment of the present disclosure, the accutase may be used.

The cultivation of the step 2) may be performed in a culturing dish on which the substrate is not coated. Further, if the culturing of the step 2) is carried out in a culturing dish having a substrate coated thereon, fixed neuronal progenitor cells may be differentiated into neuronal cells. However, when using the culturing dish without the substrate coated thereon, the neuronal progenitor cells may not be differentiated into neuronal cells. Thus, spontaneous migration of the neuronal progenitor cells may be realized, such that the neuronal progenitor cells may be re-aggregated.

Each of the re-aggregated spherical neural masses in the step 3) may have a diameter of 10 to 80 μm, in particular, 20 to 60 μm. According to one embodiment of the present disclosure, each of the spherical neural masses may be in a range of 20 to 50 μm in diameter. When the diameter of the re-aggregated spherical neural masses is about in a range of 10 to 80 μm, the re-aggregated spherical neural masses may be stripped from the bottom of the culturing dish via pipetting and then may be sub-cultured. In this connection, the sub-culturing may involve suspension culturing while replacing the culturing medium at 48 hours intervals.

When the spherical neural masses are removed from the bottom of the dish, the spherical neural masses remaining on the bottom without being aggregated may be removed from the bottom. To the contrary, the spherical neural masses that do not settle to the bottom but are suspended may be removed when the medium is replaced. The spherical neural masses have the property of constantly attaching to the culturing dishes or have the property that the spherical neural masses are constantly attached to each other. Thus, a process in which the re-aggregated spherical neural masses are removed from the bottom of the culturing dish may be repeated at intervals of 6 to 12 hours. This can prevent in advance over-coupling between the spherical neural masses. During the suspension culturing, newly formed spherical neural masses proliferate into a spherical shape and may be recovered and used when they are of a size suitable for their application purpose.

Figure 2:
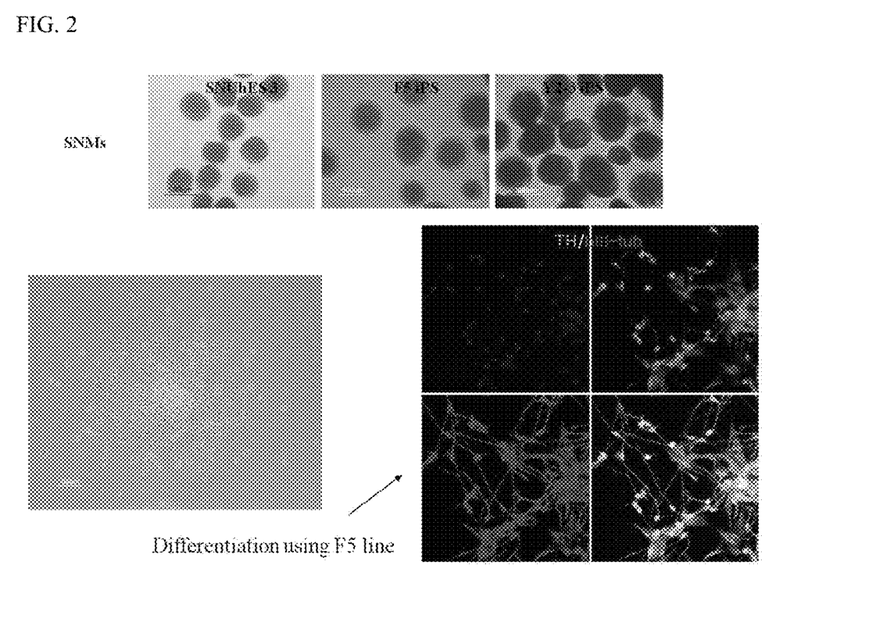
FIG. 2 checks a differentiation ability of spherical neural masses into neuronal cells via expression of a neuronal cell marker.
Figure 3:
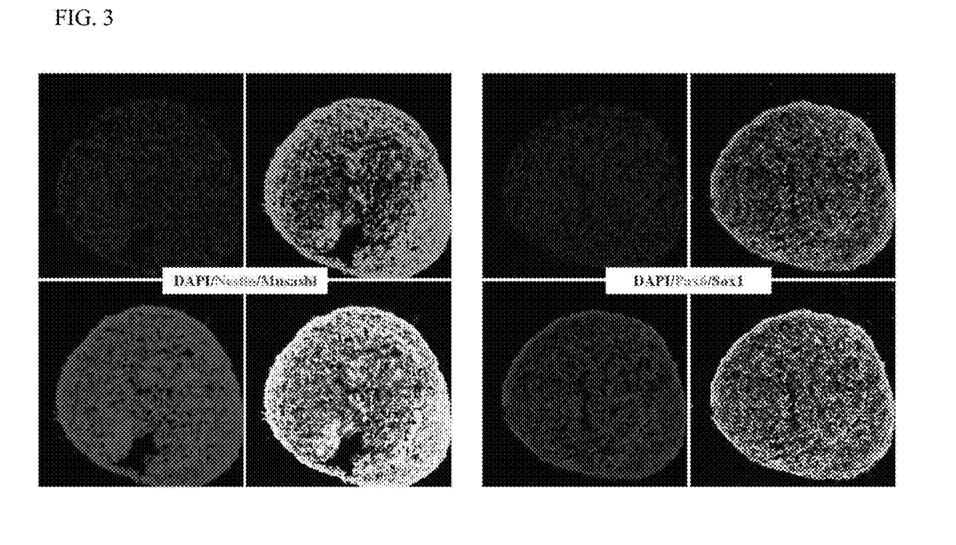
FIG. 3 checks, via immunostaining, whether a neuronal progenitor cell maker is expressed in spherical neural masses.

In a specific example according to the present disclosure, the present inventors have confirmed that when the spherical neural masses according to the present disclosure are differentiated into neuronal cells as well as neuronal progenitor cell markers, the expression of the neuronal cell markers occurs (see FIG. 2 and FIG. 3). Further, the present inventors have confirmed that when performing fragmentation and then single-cellularization of the spherical neural masses into a single cell, the spherical neural masses significantly increased the viability and recovery percentage of the cells (see FIG. 4), and, undifferentiated pluripotent stem cell markers were scarcely expressed from the re-aggregated spherical neural masses. In contrast, the present inventors have confirmed that the neuronal progenitor cell markers were strongly expressed from the re-aggregated spherical neural masses (see FIG. 6). Further, the present inventors have confirmed that the undifferentiated markers were not expressed from the re-aggregated spherical neural masses, but the neuronal progenitor cell markers were strongly expressed from the re-aggregated spherical neural masses (see FIG. 7). Moreover, the present inventors have confirmed via immunohistochemical staining that the neuronal cell markers were expressed from the adhesion-cultured spherical neural masses (see FIG. 8).

Therefore, the production method of the spherical neural masses according to the present disclosure may be used to produce the spherical neural masses having the suppressed teratoma formation.

Further, the present disclosure provides a spherical neural mass having suppressed teratoma formation, the mass being produced by the method in accordance with the present disclosure.

The method includes 1) performing single-cellularization of spherical neural masses; 2) re-aggregating the spherical neural masses single-cellularized in the step 1); and 3) recovering the spherical neural masses re-aggregated in the step 2).

In the production method, a culturing medium for the cell may be a medium supplemented with N-2 supplement, bFGF or a mixture thereof. The N-2 supplement may be added in an amount of 0.5 to 2.0% (v/v), more specifically, 1.0 to 1.5% (v/v) based on a total volume of a neuronal progenitor cell culturing medium. According to one embodiment of the present disclosure, the content of the N-2 supplement may be 1% (v/v) relative to the total volume of the neuronal progenitor cell culturing medium. Further, the bFGF may be added in a content of 0.0002 to 0.001% (w/v), more specifically 0.0006 to 0.0008% (w/v) based on the total mass of the medium for neuronal progenitor cell culturing. According to one embodiment of the present disclosure, the content of the bFGF may be 0.00063% (w/v) relative to the total mass of the medium for neuronal progenitor cell culturing.

The step 1) culturing and step 3) culturing may be performed in a culturing dish having a substrate coated thereon. The substrate may be any one or more selected from a group consisting of laminin, L-omithine, Matrigel and CeLLstart. In one embodiment according to the present disclosure, the substrate may be Matrigel.

The cultivation of the step 2) may be performed in a culturing dish on which the substrate is not coated. Thus, it is possible to induce aggregation between spherical neural mass. When using the culturing dish without the substrate coated thereon, the spherical neural masses may not be differentiated into neuronal cells. Thus, spontaneous migration of the neuronal progenitor cells may be realized, such that the neuronal progenitor cells may be re-aggregated. Further, Single-cellularization in the step 1) may involve fragmentation of the spherical neural masses using a micro fragmentation tool. In this connection, when the fragmentation is performed using a cell separation enzyme, the cell is damaged and therefore the recovery percentage is small. Thus, a physical fragmentation may be used. A tool for physical fragmentation may include any tool that can cut the mass of a diameter of 500 μm or smaller under a dissecting microscope. Specifically, the tool may include a tool fabricated by finely drawing a glass Pasteur pipette, a metal wire having a diameter of 100 μm or smaller, and a metal mesh having a hole with a micrometer (μm). According to one embodiment of the present disclosure, the fragmentation may be performed using the tool fabricated by finely drawing a glass Pasteur pipette.

Further, the fragmented spherical neural masses may be subjected to single-cellularization using, as an enzyme for cell separation, enzymes well known in the art, such as trypsin-EDTA, dispase, accutase and collagenase. According to one embodiment of the present disclosure, the accutase may be used. In addition, each of the re-aggregated spherical neural masses in the step 3) may have a diameter of 10 to 80 μm, in particular, 20 to 60 μm. According to one embodiment of the present disclosure, each of the spherical neural masses may be in a range of 20 to 50 μm in diameter.

In a specific example according to the present disclosure, the present inventors single-cellularized the spherical neural masses. Then, the single-cellularized spherical neural masses were cultured in a substrate-free medium. Thus, the spherical neural masses with the suppressed teratoma formation were produced. The present inventors have confirmed that when the spherical neural masses according to the present disclosure are differentiated into neuronal cells as well as neuronal progenitor cell markers, the expression of the neuronal cell markers occurs (see FIG. 2 and FIG. 3). Further, the present inventors have confirmed that when performing fragmentation and then single-cellularization of the spherical neural masses into a single cell, the spherical neural masses significantly increased the viability and recovery percentage of the cells (see FIG. 4), and, undifferentiated pluripotent stem cell markers were scarcely expressed from the re-aggregated spherical neural masses. In contrast, the present inventors have confirmed that the neuronal progenitor cell markers were strongly expressed from the re-aggregated spherical neural masses (see FIG. 6). Further, the present inventors have confirmed that the undifferentiated markers were not expressed from the re-aggregated spherical neural masses, but the neuronal progenitor cell markers were strongly expressed from the re-aggregated spherical neural masses (see FIG. 7).

Further, the present disclosure provides a method for differentiating neuronal progenitor cells including differentiating the spherical neural masses.

The spherical neural masses may include the features described above. Further, B27 added in place of bFGF in the differentiation may be added in an amount of 1 to 3% (v/v), more specifically 1.5% to 2.5% (v/v) based on the total differentiation medium volume. If the content of B27 is smaller than 1% (v/v), the cell differentiation efficiency may be lowered. When the content of B27 is above 3% (v/v), excessive cell differentiation and proliferation may lead to difficulty in maintenance of cell culturing. According to one embodiment of the present disclosure, the content of the B27 may be 2% (v/v).

The spherical neural masses may be sub-cultured when each mass has a diameter of 400 to 600 μm. When the sub-culturing is conducted when the diameter of each of the spherical neural masses is smaller than 400 μm, proliferation of the spherical neural masses may be delayed. When the sub-culturing is conducted when the diameter of each of the spherical neural masses is 600 μm or more, the inner cells in the spherical neural masses may be killed because of the insufficient nutrient supply. Thus, according to one embodiment of the present disclosure, when the diameter of each of the re-aggregated spherical neural masses reaches 500 μm, the re-aggregated spherical neural masses may be fragmented and sub-cultured or cryopreserved.

In a specific example according to the present disclosure, the present inventors differentiated the re-aggregated spherical neural masses into neuronal cells according to the differentiation conditions of neuronal cells. In this connection, the culturing dish coated with neuronal differentiation substrate and the medium containing B27 and free of bFGF were used. The expression of neuronal cell markers from the differentiated cells was checked by immunohistochemical staining (see FIG. 8).

Hereinafter, the present disclosure will be described in detail by the following Example.

However, the following Example is merely an exemplary illustration of the present disclosure, and the content according to the present disclosure is not limited thereto.

<Example 1> Preparation for Culturing of Neuronal Progenitor Cells

According to the present disclosure, only neuronal progenitor cells were isolated from fragments of spherical neural masses formed from pluripotent stem cells, via reformation process of the spherical neural masses.

<1-1> Production of Medium for Cultivation of Neuronal Progenitor Cells

First, a basic medium for neuronal progenitor cells was produced by adding 5 ml of 0.1 mM non-essential amino acids (NEAA) and 5 ml of 2 mM P/S (penicillin/streptomycin) to 490 ml of DMEM (F12). After mixing the produced medium well, the mixed medium was filtered using a filter with a pore size of 0.22 μm and a vacuum pump, and then was dispensed by 49 ml into 50 ml tubes. The tube was sealed with a paraffin film and was kept at 4° C. When the amount of medium was smaller than 12 ml, it was stored in a 15 ml tube. When the amount was greater than or equal to 12 ml, it was stored in a 50 ml tube.

The culturing medium for the neuronal progenitor cells was prepared by adding 0.5 ml of 1% N-2 supplement and 0.4 ml of 80 μg/ml basic fibroblast growth factor (bFGF) into the above prepared basic medium.

<1-2> Preparation of Dish for Culturing Neuronal Progenitor Cells

The size of the dish for culturing the neuronal progenitor cells depends on the number of the spherical neural masses. In this example, 10 spherical neural masses fragmented per a 35 mm diameter sized culturing dish were used (1 aggregate/cm$^2$). The culturing dish containing 1 ml of 20-fold diluted Matrigel was stored at room temperature for 1 hour before use.

<Example 2> Checking Spherical Neural Masses

<2-1> Checking Differentiation Ability of Spherical Neural Masses to Neuronal Cells First, spherical neural masses to be used in the experiment were immunostained to check whether the cells could differentiate into neuronal cells.

Spherical neural masses were produced from human embryonic stem cell line (SNUhES3) and induced pluripotent stem cell line (F5 iPS, Y2-3 iPS) as follows. The human embryonic stem cell lines (SNUhES3) and induced pluripotent stem cell lines (F5 iPS, Y2-3 iPS) were proliferated in 7 days of culturing and were mechanically divided into lumps having 200-300 cells which in turn were cultured on support cells. Next, the lumps were subjected to treatment with 2 mg/ml collagenase (collagenase IV; Invitrogen, Carlsbad, Calif., USA) at 37° C. for 40 minutes, such that stem cell colonies were removed therefrom. The resulting product was input into a culturing dish for microbial culturing and was subjected to suspension culturing in bFGF-free stem cell culturing medium for 7 to 21 days, such that embryoid bodies (EB) were prepared. After removal of the cystic embryoid body (cystic EB) with a cystic form from the embryoid body. The remaining embryoid body was attached to a culturing dish treated with Matrigel® (BD, Franklinlakes, N.J., USA) and then was cultured in a stem cell culturing medium supplemented with 1×N-2 supplement for 5 days. Thus, the spherical neural masses were selectively produced.

Further, for immunostaining experiments, the spherical neural masses were fragmented using the tool manufactured by thinly drawing a glass Pasteur pipette. The fragmented spherical neural masses were cultured on a glass cover glass coated with differentiating substrate. The culturing medium was a medium for neuronal cell differentiation containing N2 and B27. After 2 weeks of cultivation, we examined whether cells expressing the neuronal cell marker beta-III-tubuline (bIII-tub) and tyrosine hydroxylase (TH), a marker of dopaminergic neuronal cell as a blast cell of differentiated neuronal cells, were observed. Samples were treated with 3% formalin solution for 20 minutes and stored in phosphate buffer. Prior to the treatment of the antibody, the samples were treated with blocking solution (2% bovine serum albumin, Sigma) for one day. The samples reacted with the primary antibody for 12 hours, and with the secondary antibody for 1 hour. Then, the samples were sealed with fluorescence preservation solution containing DAPI, and were observed with a confocal fluorescence microscope (Nikon, Japan). In this connection, rabbit anti-beta III tubulin antibody (1:100, Chemicon) and mouse anti-TH (1:200, Chemicon) were used as primary antibodies for immunological staining. Alexa Fluor 488 donkey anti-mouse IgG and Alexa Fluor 594 donkey anti-rabbit IgG (1:200, Molecular Probes, USA) were used as secondary antibodies. As a result, as shown in FIG. 2, tyrosine hydroxylase (TH) as a marker of the dopaminergic neuronal cell and b III-tub (beta 3 tubuline) as the neuronal cell marker were expressed from the spherical neural masses (see FIG. 2).

<2-2> Checking Expression of Neuronal Progenitor Cell Marker from Spherical Neural Masses Further, whether the spherical neural masses express neuronal progenitor cell markers were checked by immunostaining. The spherical neural masses were frozen and fragmented and then attached to a cover glass for immunostaining. The immunostaining method was performed under the same conditions and method as the Example <2-1>. In this connection, for immunostaining, rabbit anti-Musashi antibody (1:100, Chemicon), rabbit anti-Sox1 antibody (1:200, Milipore), mouse anti-human Nestin antibody (1:200, Chemicon) and mouse anti-Pax6 antibody (1:500, Novus Biologicals) were used as primary antibodies. Alexa Fluor 488 donkey anti-mouse IgG and Alexa Fluor594 donkey anti-rabbit IgG (1:200, Molecular Probes, USA) were used as secondary antibodies.

As shown in FIG. 3, neuronal progenitor cell markers nestin, Musashi and Pax6 were expressed from the spherical neural masses (FIG. 3).

<Example 3> Production of Spherical Neural Masses

<3-1> Fragmentation (Schizolysis) of Spherical Neural Masses

First, the spherical neural masses were fragmented to a size such that a volume thereof is no more than 100 μm³ using a micro fragment tool. Specifically, the spherical neural masses were fragmented using a thin strip of the glass Pasteur pipette. The fragmented spherical neural masses were adhesion-cultured for 12 hours at 37° C. and 5% $CO_2$ using the Matrigel-coated culturing dish and the neuronal progenitor cell culturing medium of Example 1.

<3-2> Checking Single-Cellularization of Fragmented Spherical Neural Masses and Cell Viability Thereof Single-Cellularization of Fragmented Spherical Neural Masses The fragmented spherical neural masses were single-cellularized by the following method.

First, the medium of the spherical neural masses cultured in the Section <3-1> were removed and washed lightly with PBS (phosphate buffered saline). After the PBS was removed, an accutase of 0.2 ml/cm² was added thereto. The fragments of spherical neural masses attached via reaction at 37° C., 5% $CO_2$ for 40 to 60 minutes were single-cellularized. After the spherical neural masses were collected by centrifugation, the accutase was removed therefrom. The spherical neural masses were washed with a medium for neuronal progenitor cell culturing and then were input to 1 ml of the culturing medium and were counted.

Checking Increase of Cell Viability According to Process Change of Single-Cellularization Next, we checked whether the fragmentation and single-cellularization of the spherical neural masses affected the cell viability and recovery percentage.

Specifically, the single-cellularized cells were subjected to adhesion-culturing for 1 day and then were single-cellularized again. The cells were stained with trypan blue. Then, Cell number and viability of the stained cells stained with trypan blue were measured by automatic cell counter. Further, a control group was compared therewith under the same conditions. The control group refers to the cell group treated with enzyme treatment with fragmentation and then without adhesion-culturing.

Figure 4:
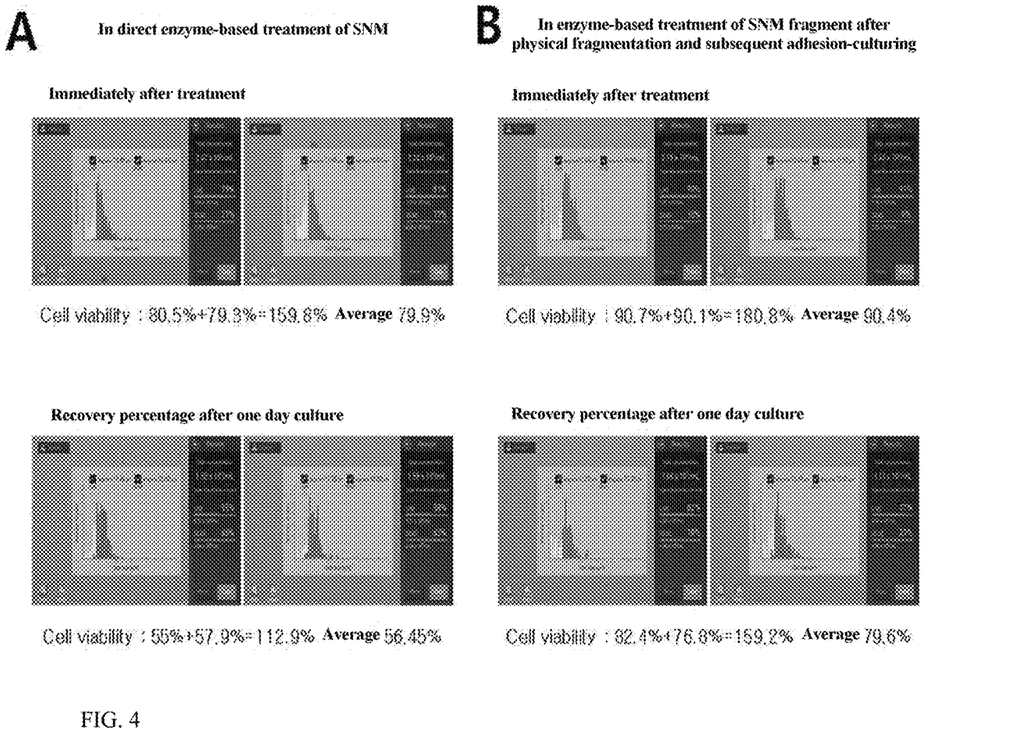
FIG. 4 is a graph of a viability of (A) cells when spherical neural masses are single-cellularized with a conventional method using enzyme and a viability of (B) cells when spherical neural masses are subjected to an enzyme treatment by fragmentation and then adhesion-culturing.

As a result, as shown in FIG. 4, the cell viability and recovery percentage of the spherical neural masses after the spherical neural masses were fragmented and adhesion-cultured and single-cellularized were greatly increased.

<3-3> Induction of Spontaneous Re-Aggregation of Single-Cellularized Cells

The cells single-cellularized in the Section <3-2> were treated in the following manner to be re-aggregated again spontaneously.

First, the single-cellularized cells were diluted in the neuronal progenitor cell culturing medium at a concentration of $5.5 \times 10^4$ cells/0.2 ml/cm² and were cultured at 37° C. and 5% $CO_2$ for 24 hours. In this connection, in order to spontaneously re-aggregate spherical neural masses without being differentiated into neuronal cells, the spherical neural masses were cultured in a culturing dish without the substrate coated thereon. After 24 hours, the masses were first pipetted and suspended. Then, an approach in which using a pipetting method, the mass is removed from the bottom of the culturing dish was repeated until the diameter of the cell aggregate reaches at least about 20 μm and not larger than 50 μm. In this connection, while the culturing medium was replaced at 48 hours intervals, suspension culturing was performed. When the mass was removed from the bottom, the cells which were not aggregated but were remaining on the bottom were removed from the bottom. Only the mass was settled on the bottom and the suspended cells were removed while the medium was replaced. Since aggregates maintain the properties of attaching to culturing dishes and to other aggregates, the re-aggregated aggregates were subjected to the same method at least every 12 hours, thus to prevent excessive binding of the mass to the culturing dish or another aggregate.

Figure 5:
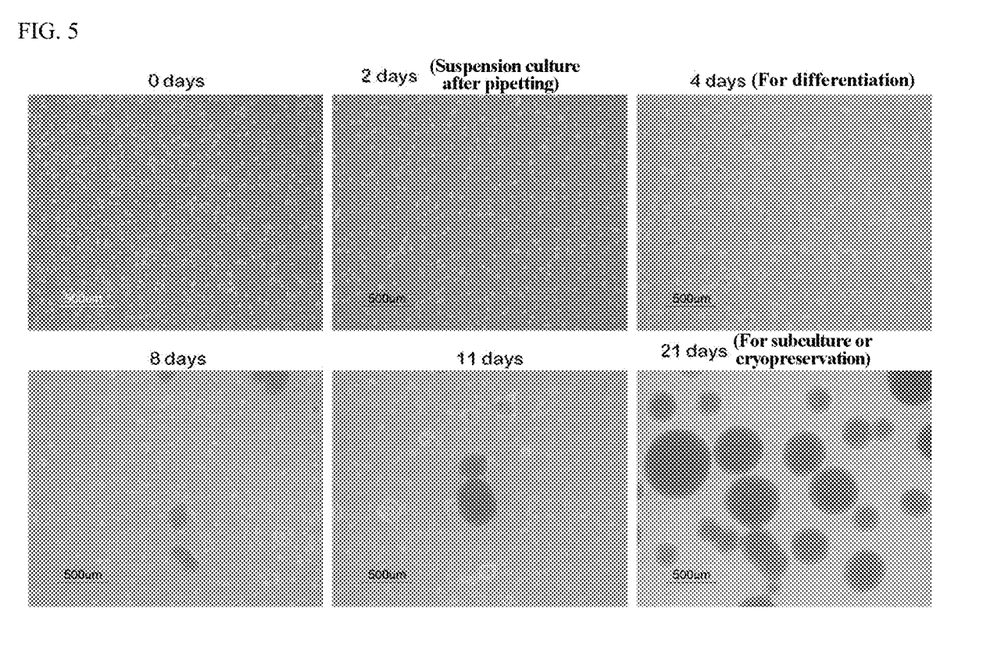
FIG. 5 shows changes in a size and shape of the mass in the culturing dish during spontaneous aggregation of spherical neural masses after single-cellularization thereof.

As a result, as shown in FIG. 5, it was checked that the shape and size of the masses formed by re-aggregating the cells over the culturing time after the single-cellularization thereof were changed. This re-aggregated spherical neural masses were recovered at appropriate times according to the size of the mass. The recovered spherical neural masses may be used for differentiation (4th day), sub-culturing, or cryo-preservation (21st day).

<3-4> Differentiation of Re-Aggregated Spherical Neural Masses

When the diameter of each of the spherical neural masses re-aggregated in the <3-3> was between 50 μm and 100 μm, the spherical neural masses were recovered to induce differentiation thereof into neuronal cells.

Specifically, all of the re-aggregated spherical neural masses for differentiation were recovered and suspended in the neuronal progenitor cell culturing medium. The spherical neural masses then were transferred to a culturing dish having a 2.5 to 3 times area or 3 culturing dishes of the same area to differentiate the spherical neural masses. A 6 cm diameter sized culturing dish was used during re-aggregation. All of the re-aggregated spherical neural masses were recovered and then were suspended in 15 ml of the culturing medium and were transferred to a 75 cm² T-flask for differentiation. For differentiation, a dish coated with Matrigel was used as in Example 1. After 24 hours of culturing, the medium was replaced with a medium supplemented with 2% (v/v) B27 instead of bFGF, thus to induce differentiation thereof into neuronal cells. When the re-aggregated spherical neural masses not used for differentiation reach 500 μm in diameter, they were fragmented and either sub-cultured or cryopreserved.

<Experimental Example 1> Checking Characteristics of Re-Aggregated Spherical Neural Masses We checked whether the cells of the re-aggregated spherical neural masses maintained the characteristics of spherical neural masses.

<1-1> Flow Cytometry

First, the spherical neural masses were single-cellularized by treatment with accutase. Then, the cells were washed with PBS, fixed with a fixative solution, and immunostained. The presence or absence of non-differentiated cells was checked via the staining of SSEA-4 and TRA-61 proteins, as well-known markers of non-differentiated pluripotent stem cells. The purity of neuronal progenitor cells was checked using Musashi and Pax6 proteins, which are markers of the neuronal progenitor cells. As a control group, human embryonic stem cells (ES) were used. We compared the conventional neuronal precursor group (SNM) with the re-formed spherical neural masses (Reformed SNM) together with the control group.

Figure 6:
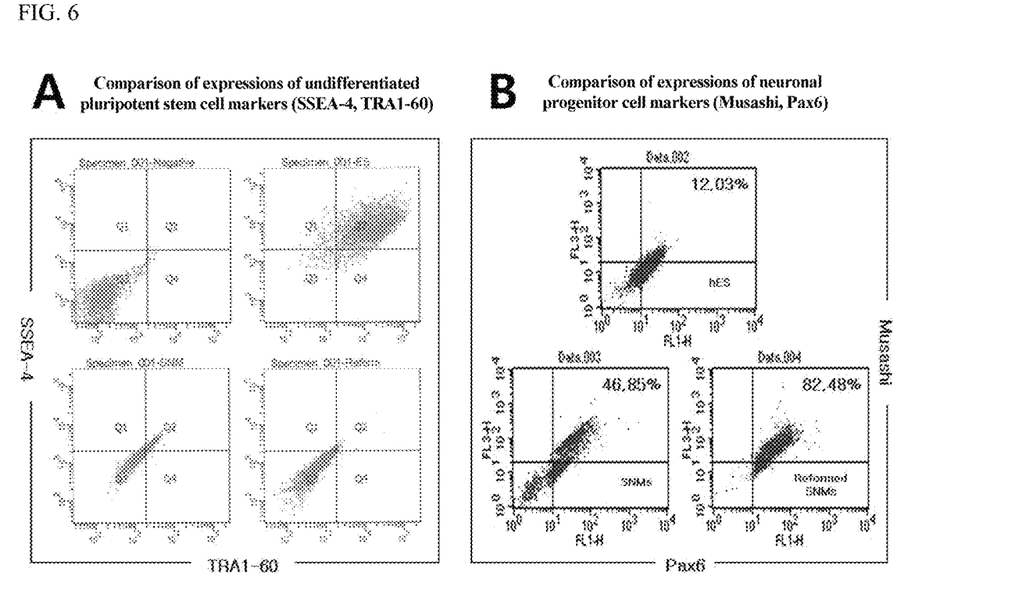
FIG. 6 shows a graph for checking, via flow cytometry, expression of undifferentiated pluripotent stem cell marker (A) and neuronal progenitor cell marker (B) from embryonic neuronal progenitor cells (SNM), and re-aggregated spherical neural masses (Reform).

As a result, as shown in FIG. 6, SSEA-4 and Tra1-60 proteins, as undifferentiated pluripotent stem cell markers mainly expressed from embryonic stem cells, were rarely expressed from the re-aggregated spherical neural masses (FIG. 6A). To the contrary, Musashi and Pax6, as the neuronal progenitor cells marker, were expressed from most of the cells constituting the re-aggregated spherical neural masses. Compared with the conventional SNM, in the re-formed spherical neural masses (Reformed SNM), only cells strongly expressing the neuronal progenitor cell markers were observed as a single cell group (FIG. 6B). These results indicate that the re-aggregated spherical neural masses serve to remove the undifferentiated cells and may be purely separated into cells in the same differentiation step.

<1-2> RT-PCR

We observed changes in gene expression from human embryonic stem cells, embryoid bodies, spherical neural masses and re-aggregated spherical neural masses, respectively, via RT-PCR. Expression of the gene was checked using Oct4 and Nanog, which are mainly expressed from undifferentiated stem cells as a marker, using Sox1, Pax6 and nestin, which are mainly expressed from spherical neural masses as makers, and using NF-M, which is mainly expressed from early neuronal cells as makers.

Specifically, RNAs of cells were extracted with TRIzol solution (Invitrogen) from human embryonic stem cells, embryoid bodies, spherical neural masses of the Example 2, and re-aggregated spherical neural masses of the section <3-3>, respectively. cDNA was synthesized using a cDNA reverse kit (AccuPower RT PreMix; Bioneer). While using the synthesized cDNA as a template, RT-PCR was performed using a primer for each of Oct4, Nanog, Sox1, Pax6, nestin and NF-M, and Taq polymerase (HiPi Plus 5×PCR Premix; Elpis biotech, Taejeon, Korea). The primer base sequences used in the RT-PCR are shown in Table 1 below.

TABLE 1

| Gene name | Gene direction | (SEQ ID No) | Base sequence |
|---|---|---|---|
| Gapdh | Forward | (SEQ ID No. 1) | 5'-ACCACAGTCCATGCCATCAC-3' |
|  | Reverse | (SEQ ID No. 2) | 5'-TCCACCACCCTGTTGCTGT-3 |
| 04-Oct | Forward | (SEQ ID No. 3) | 5'-CGTTCTCTTTGGAAAGGTGTTC-3' |
|  | Reverse | (SEQ ID No. 4) | 5'-ACACTCGGACCACGTCTTTC-3' |
| Nanog | Forward | (SEQ ID No. 5) | 5'-GCGTACGCAAATTAAAGTCCAGA-3' |
|  | Reverse | (SEQ ID No. 6) | 5'-TGCTATTCTTCGGCCAGTTG-3' |
| Pax6 | Forward | (SEQ ID No. 7) | 5'-GGCAACCTACGCAAGATGGC-3' |
|  | Reverse | (SEQ ID No. 8) | 5'-TGAGGGCTGTGTCTGTTCGG-3' |
| Sox1 | Forward | (SEQ ID No. 9) | 5'-CAATGCGGGGAGGAGAAGTC-3' |
|  | Reverse | (SEQ ID No. 10) | 5'-CTCTGGACCAAACTGTGGCG-3' |
| Nestin | Forward | (SEQ ID No. 11) | 5'-CAGCTGGCGCACCTCAAGATG-3' |
|  | Reverse | (SEQ ID No. 12) | 5'-AGGGAAGTTGGGCTCAGGACTGG-3' |
| NF-M | Forward | (SEQ ID No. 13) | 5'-GAGCGCAAAGACTACCTGAAGA-3' |
|  | Reverse | (SEQ ID No. 14) | 5'-CAGCGATTTCTATATCCAGAGCC-3' |

Figure 7:
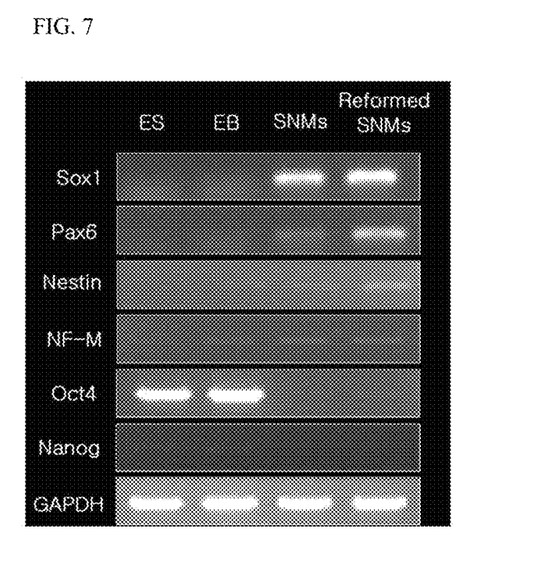
FIG. 7 shows a diagram for checking, via RT-PCR, whether undifferentiated markers and neuronal progenitor cell markers are expressed from re-aggregated spherical neural masses.

As a result, as shown in FIG. 7, undifferentiated markers were not expressed from re-aggregated spherical neural masses. However, expression of the neuronal progenitor cell markers from the re-aggregated spherical neural masses was increased.

<1-3> Immunohistochemical Staining

Immunohistochemical staining was performed to check whether the differentiation ability of the re-aggregated spherical neural masses was maintained.

The re-aggregated spherical neural masses of the Section <3-3> were fragmented using a tool fabricated by heating and finely drawing the glass Pasteur pipet. The fragmented spherical neural masses were attached to a glass cover glass coated with Matrigel, the same substrate as in Example 1, and then were cultured in the neuronal progenitor cell culturing medium for 1 day, and cultured for 6 days in medium for neuronal cell differentiation. The attached glass cover glasses were collected on the 2nd and 7th days of culturing. The samples were treated with 3% formalin solution for 20 minutes and stored in phosphate buffer. The samples were treated with blocking solution (2% bovine serum albumin, Sigma) for one day prior to antibody treatment. The primary antibody was reacted with the samples for 12 hours and the secondary antibody was reacted with the samples for 1 hour. After sealing the samples with fluorescence preservation solution containing DAPI, the samples were observed using a confocal fluorescence microscope (Nikon, Japan). In this connection, for immunological staining, rabbit anti-beta III tubulin antibody (1:100, Chemicon), mouse anti-human Nestin antibody (1:200, Chemicon), mouse anti-TH antibody (1:200, Chemicon), and mouse anti-GABA antibody (1:200, Chemicon) were used as the primary antibody. Alexa Fluor 488 donkey anti-mouse IgG, Alexa Fluor 594 donkey anti-rabbit IgG and Alexa Fluor 488 donkey anti-rabbit IgG (above 1:200, Molecular Probes, USA) were used as the secondary antibodies.

Figure 8:
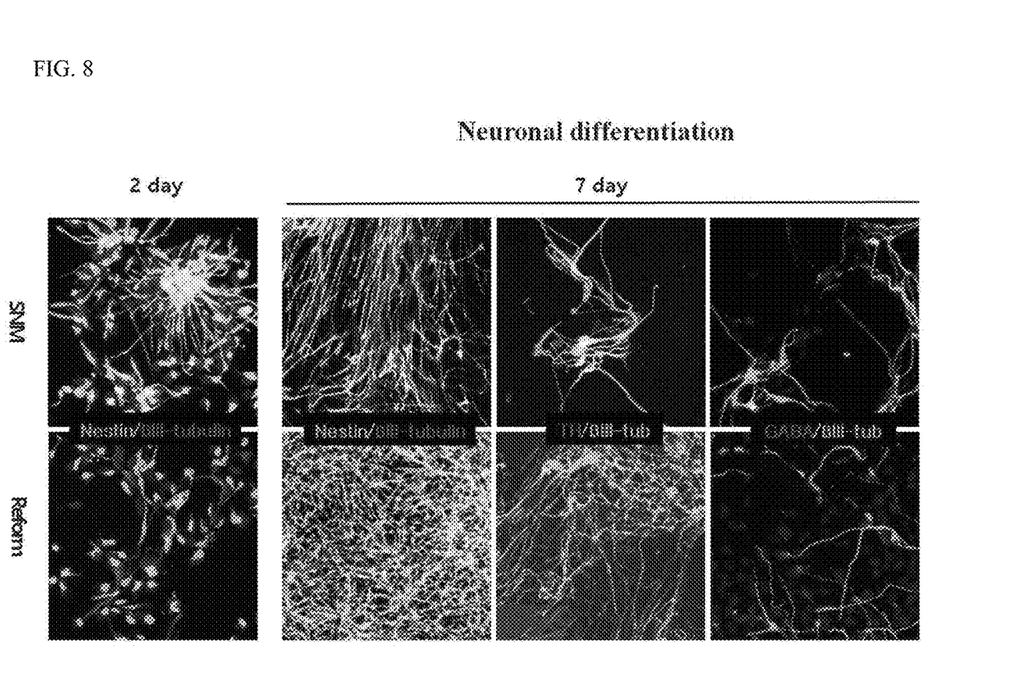
FIG. 8 shows a diagram for checking, via immunohistochemical staining, whether differentiation ability of re-aggregated spherical neural masses is maintained.

As a result, as shown in FIG. 8, beta-III-tubulin, TH and gaba protein, which are the markers of the differentiated neuronal cells, were expressed from the re-aggerated spherical neural masses differentiated for 7 days after the adhesion-culturing as expressed from the existing neuronal progenitor cells. Thus, we confirmed that the re-aggregated spherical neural masses retain their differentiation ability.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for producing spherical neural masses having suppressed teratoma formation, the method including the following steps:
   1) fragmentation of the spherical neural masses to obtain fragmented spherical neural masses;
   2) adhesion-culturing of the fragmented spherical neural masses in a culturing dish comprising culturing medium for neuronal progenitor cell to obtain adhesion-cultured spherical neural masses;
   3) performing single-cellularization of the adhesion-cultured spherical neural masses by adding enzyme to obtain single cells;
   4) inducing spontaneous aggregation of cells by adhesion-culturing of the single cells of step 3) in a culturing dish without an additional substrate coated thereon and without adding a differentiation-inducing factor to obtain aggregates attached to a bottom of the culturing dish;
   5) removing floating cells after step 4) and inducing spontaneous re-aggregation of single cells by repeatedly suspending the aggregates attached to the bottom of culturing dish to obtain re-aggregated spherical neural masses; and
   6) recovering the spherical neural masses re-aggregated in step 5), wherein the re-aggregated spherical neural masses contain fewer undifferentiated cells compared to the spherical neural masses in step 1).

2. The method of claim 1, wherein the culturing medium for neuronal progenitor cell comprise N-2 supplement, bFGF, or a mixture thereof.

3. The method of claim 2, wherein the N-2 supplement is added in a content of 0.5 to 2.0% (v/v) based on a total volume of the culturing medium.

4. The method of claim 2, wherein the bFGF is added in a content of 0.0002 to 0.001% (w/v) based on a total mass of the culturing medium.

5. The method of claim 1, wherein the step 2) is performed in a culturing dish having a substrate coated thereon, wherein the substrate includes at least one selected from a group consisting of laminin, L-ornithine, and Matrigel.

6. The method of claim 1, wherein each of the re-aggregated spherical neural masses of the step 6) has a diameter in a range of 10 μm to 80 μm.

7. A method for differentiating spherical neural masses into neuronal cells, the method including the following steps:
   1)-6) performing steps 1) to 6) of claim 1 to obtain recovered re-aggregated spherical masses; and
   7) differentiating the recovered re-aggregated spherical neural masses into neuronal cells.

8. The method of claim 7, wherein the differentiating in the step 7) is carried out in a medium supplemented with B27 instead of bFGF.

9. The method of claim 8, wherein the B27 is added in a content of 1 to 3% (v/v) based on a total volume of the medium.

10. The method of claim 7, wherein the spherical neural masses are sub-cultured when each of the spherical neural masses has a diameter equal to or larger than 500 μm.

* * * * *